US012115359B2

(12) United States Patent
Boström

(10) Patent No.: US 12,115,359 B2
(45) Date of Patent: Oct. 15, 2024

(54) MEDICAMENT DELIVERY DEVICE

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 829 days.

(21) Appl. No.: 15/734,290

(22) PCT Filed: Jun. 28, 2019

(86) PCT No.: PCT/EP2019/067424
§ 371 (c)(1),
(2) Date: Dec. 2, 2020

(87) PCT Pub. No.: WO2020/015984
PCT Pub. Date: Jan. 23, 2020

(65) Prior Publication Data
US 2021/0220564 A1      Jul. 22, 2021

(30) Foreign Application Priority Data

Jul. 20, 2018  (EP) .................................... 18184846

(51) Int. Cl.
*A61M 5/32* (2006.01)
(52) U.S. Cl.
CPC ................................. *A61M 5/3202* (2013.01)
(58) Field of Classification Search
CPC .......................... A61M 5/3204; A61M 5/3202
See application file for complete search history.

(56) References Cited

U.S. PATENT DOCUMENTS

| 11,389,636 | B2* | 7/2022 | Coyle | A61M 39/16 |
| 2016/0067422 | A1* | 3/2016 | Davis | A61M 5/3134 |
| | | | | 604/192 |
| 2018/0304067 | A1* | 10/2018 | Ryan | A61M 39/1011 |
| 2021/0268202 | A1* | 9/2021 | Boström | A61M 5/3213 |

FOREIGN PATENT DOCUMENTS

| EP | 3030287 A1 | 6/2016 |
| WO | 2015/169608 A1 | 11/2015 |
| WO | 2016/202555 A1 | 12/2016 |
| WO | WO-2017102175 A1 * | 6/2017 | .......... A61M 5/2033 |

OTHER PUBLICATIONS

International Search Report and Written Opinion for Int. App. No. PCT/EP2019/067424, mailed Feb. 12, 2020.

* cited by examiner

*Primary Examiner* — William R Carpenter
(74) *Attorney, Agent, or Firm* — McDonnell Boehnen Hulbert & Berghoff LLP

(57) ABSTRACT

A protective cap is presented that is releasably connected to a medicament delivery device, which medicament delivery device is provided with an activator element at a proximal end thereof, the protective cap has first positive holding elements arranged on an inner surface of the protective cap, which first holding elements are designed to interact with second holding elements, arranged on an outer surface of the activator element of the medicament delivery device.

7 Claims, 11 Drawing Sheets

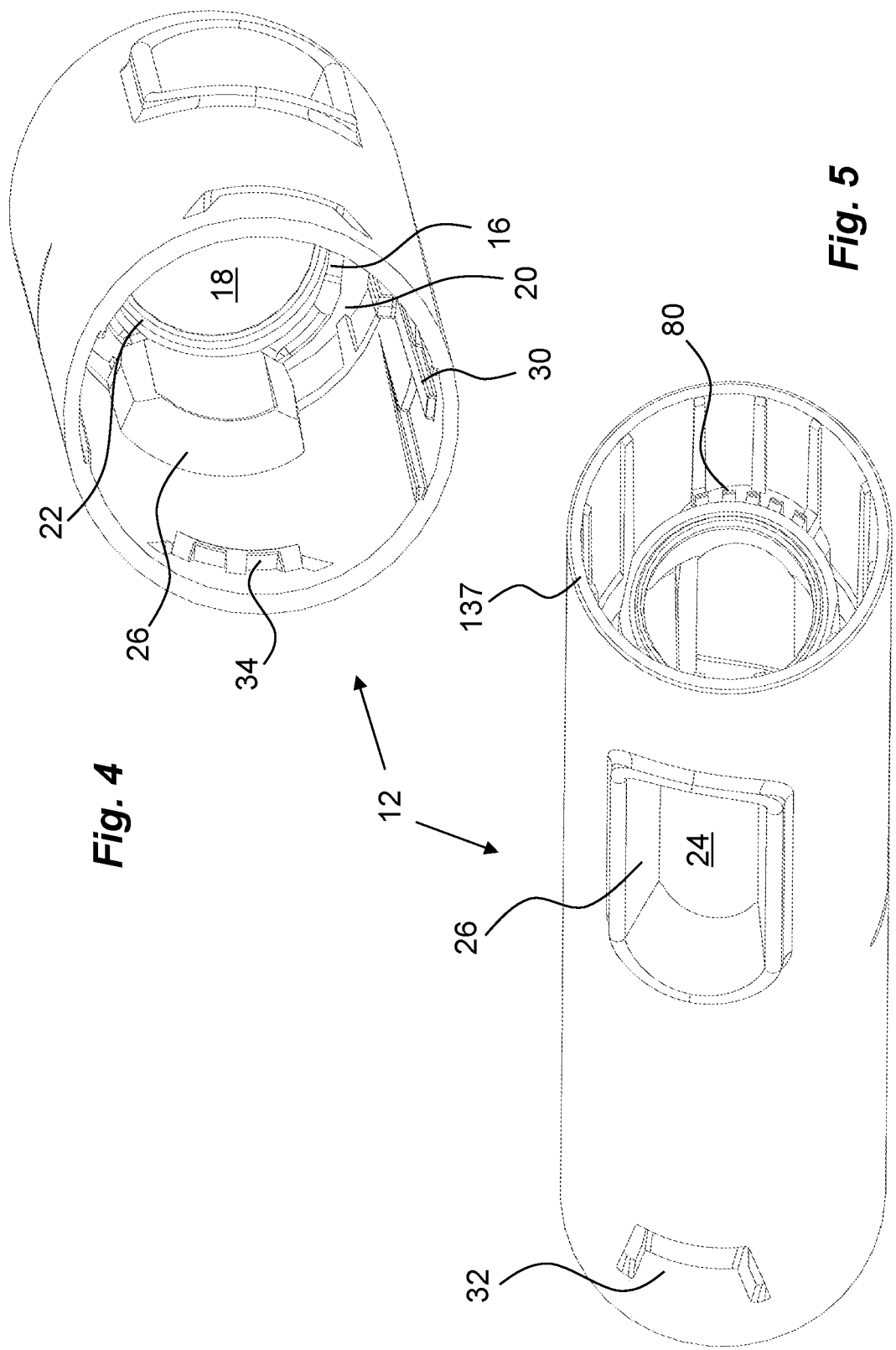

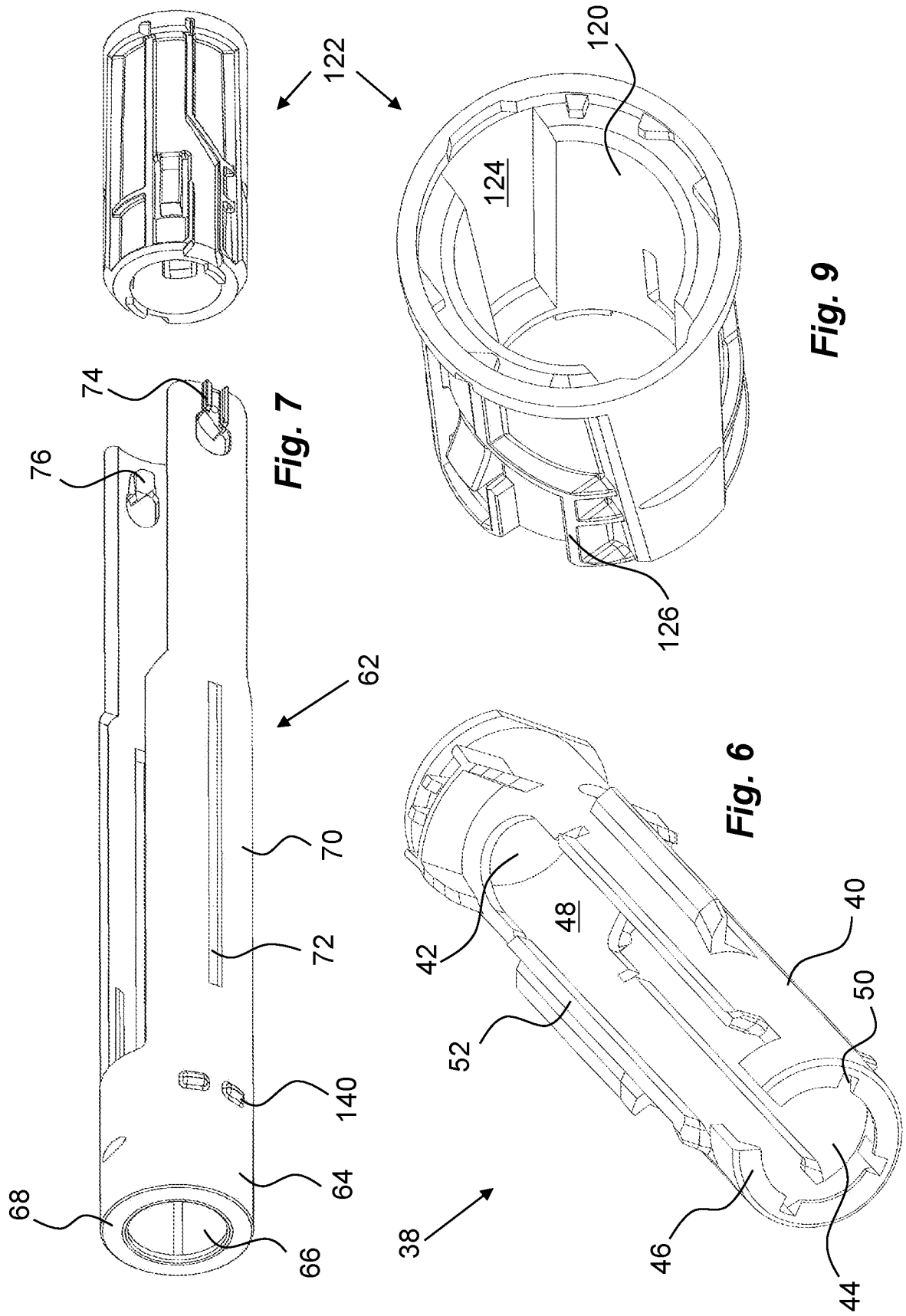

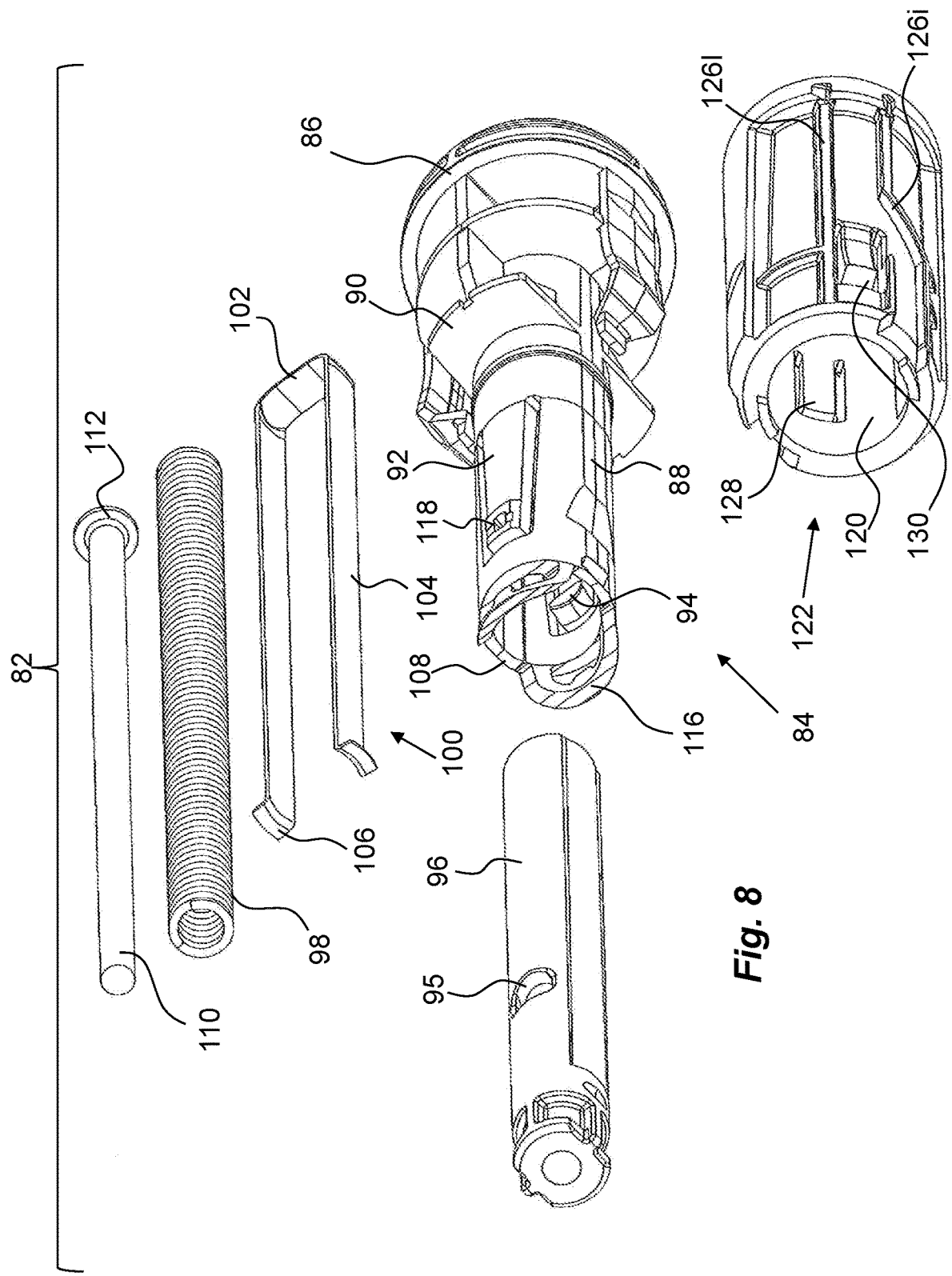

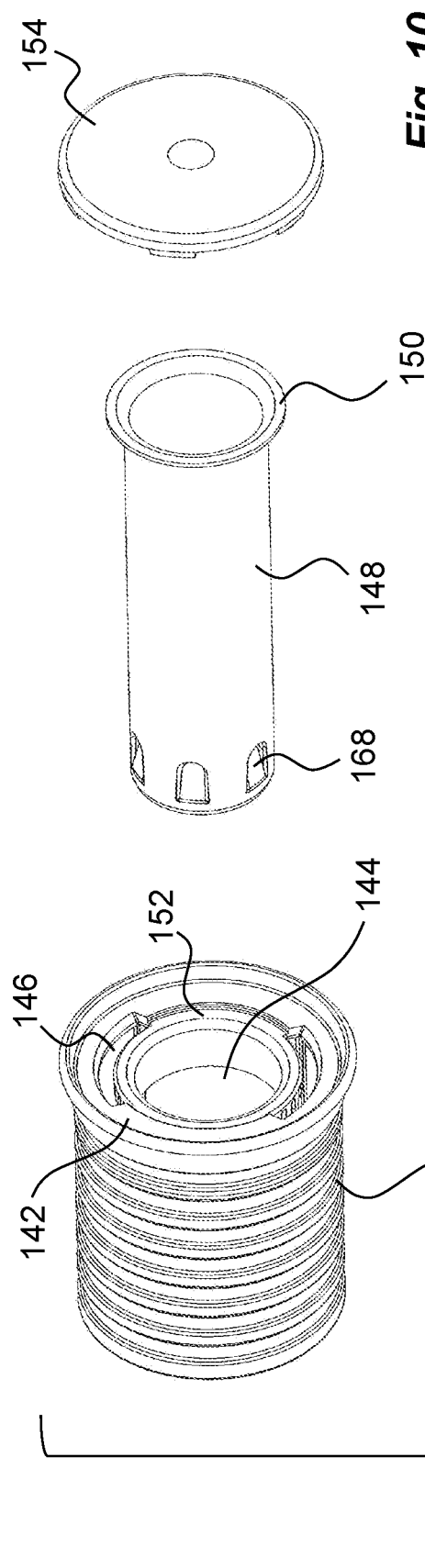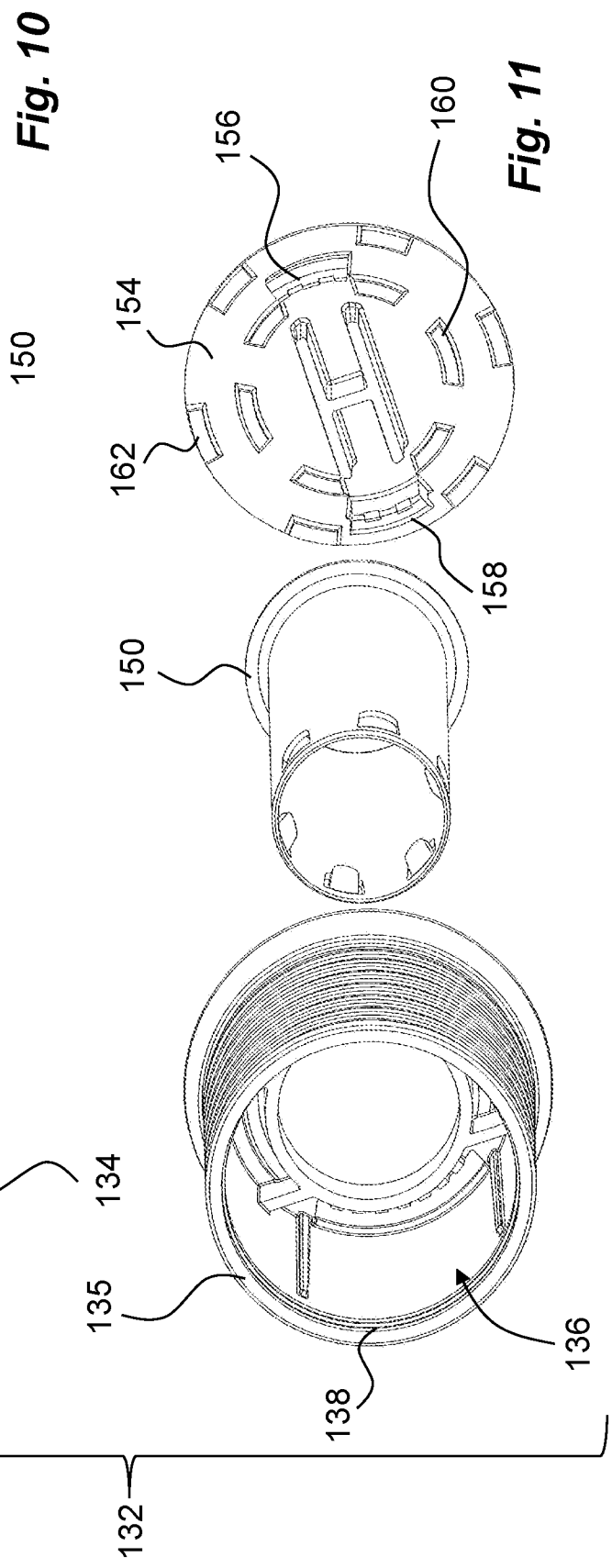

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2019/067424 filed Jun. 28, 2019, which claims priority to European Patent Application No. 18184846.6 filed Jul. 20, 2018. The entire disclosure contents of these applications are herewith incorporated by reference into the present application.

TECHNICAL AREA

The present application relates to a medicament delivery device comprising a safety cap that on the one hand protects a dose delivery member of the medicament delivery device and on the other hand removes protective elements surrounding a medicament delivery member of the medicament delivery device.

BACKGROUND

A large number of medicament delivery devices on the market and developed during the last 20 years are arranged with a protective cap at the proximal end thereof that on the one hand protect the proximal end of the medicament delivery device, which proximal end is arranged with a dose delivery member such as an injection needle. The injection needle for instance has to be kept sterile before use, whereby it is surrounded by a covering material such as a sheath of e.g. rubber, creating a so called flexible needle shield or FNS. Further developments in that regards are the so called rigid needle shields or RNS's that have an outer shell of a more rigid material surrounding the flexible inner sheath. The main purpose in any event is to keep the injection needle protected and sterile.

The safety cap on the other hand usually has two functions, to protect the medicament delivery member and other elements at the proximal end of the medicament delivery device and on the other hand provide an aid for removing the medicament delivery member shield when the medicament delivery device is to be used. It is designed to facilitate for a user to pull off the safety cap and at the same time the medicament delivery member shield.

However, many of the medicament delivery devices developed have a number of automatic features that will be automatically activated upon use by a patient or user. One such automatic feature is the activation of an injection when a medicament delivery device is pressed against a dose delivery site. This is often done in that a medicament delivery member guard is pushed into the housing of the medicament delivery device when the medicament delivery device is pressed against the dose delivery site, and distal linear movement of the medicament delivery member guard in relation to a housing of the medicament delivery device. The movement of the medicament delivery member guard causes a power unit to be activated and initiate and perform an injection of a dose of medicament at the medicament delivery site.

The solution with a slidable or movable medicament delivery member guard at the proximal end has some risks entailed. For instance, if the medicament delivery device is dropped onto a hard surface such if a user drops the medicament delivery device onto a floor, there is a risk that the medicament delivery member guard is moved distally due to the impact forces on the medicament delivery device. This unintentional movement may in turn cause the power pack to be activated before the medicament delivery device is ready to the used and even without the safety cap and the medicament delivery member guard removed, rendering the medicament delivery device useless for a patient. Especially if the medicament is crucial for a patient, such an occurrence may be very serious if the patient has no additional medicament delivery devices.

There is thus a need for such a type of devices to have additional safety features, minimizing the risk of unintentional activation if the medicament delivery device is suddenly dropped or in any other way exposed to sudden impact forces.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The aim of the present application is to remedy the drawbacks of the state of the art devices. This aim is solved by a protective safety cap arrangement comprising the features of the independent claim. Preferably embodiments of the present application form the subject of the dependent claims.

According to one aspect, a protective cap is provided that is to be releasably connected to a medicament delivery device, where the medicament delivery device may be provided with an activator element at a proximal end thereof. The activator may be a component or element that is movable when the medicament delivery device is for example pressed or held against a dose delivery site. In this regard the activator element may be a medicament delivery member guard such as a needle shield or the like that can be operably connected to a power unit of the medicament delivery device which in turn may be arranged to perform different functions of the medicament delivery device such as penetration, injection, withdrawal if the medicament delivery device is an injection device.

The protective cap may comprise a first holding element or elements arranged on a first surface of the protective cap, wherein the first holding elements are designed to interact with a second holding element or elements arranged on a second surface of the activator element, wherein the first and the second surfaces are facing each other.

As an example the first surface may be an inner surface of protective cap and the second surface may be an outer surface of the activator element of the medicament delivery device. Alternatively, the first surface may be an outer surface of protective cap and the second surface may be an inner surface of the activator element of the medicament delivery device.

As one feasible solution, the first holding element may comprise protruding elements and the second holding element may comprise protruding elements. The protective cap may further comprise abutment surfaces that are to interact with fixed abutment surfaces of the medicament delivery device in order to define the position of the protective cap in relation to the medicament delivery device when attached.

According to one feasible solution, either of the first and the second holding elements comprise protruding elements and wherein respective at least one of other in the pair the first and the second holding elements comprise recess elements. The first or second protruding elements may comprise discrete elements or as an alternative may comprise continuous element or elements.

According to a further aspect, the protective cap may comprise openings in the proximal area of the protective cap for forming air passages through the protective cap. In this regard, the protective cap may comprise a generally tubular body and a lid attached to the proximal end, and spacers arranged between the body and the lid for creating the air passages. Further, the lid may be used for holding a medicament delivery member shield remover that may be arranged in the protective cap.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 4 is a detailed view of components comprised in the medicament delivery device of FIG. 1, FIG. 5 is a detailed view of components comprised in the medicament delivery device of FIG. 1, FIG. 6 is a detailed view of components comprised in the medicament delivery device of FIG. 1, FIG. 7 is a detailed view of components comprised in the medicament delivery device of FIG. 1, FIG. 8 is a detailed view of components comprised in the medicament delivery device of FIG. 1, FIG. 9 is a detailed view of components comprised in the medicament delivery device of FIG. 1, FIG. 10 is a detailed view of components comprised in the medicament delivery device of FIG. 1, FIG. 11 is a detailed view of components comprised in the medicament delivery device of FIG. 1.

DETAILED DESCRIPTION

Figure 3:
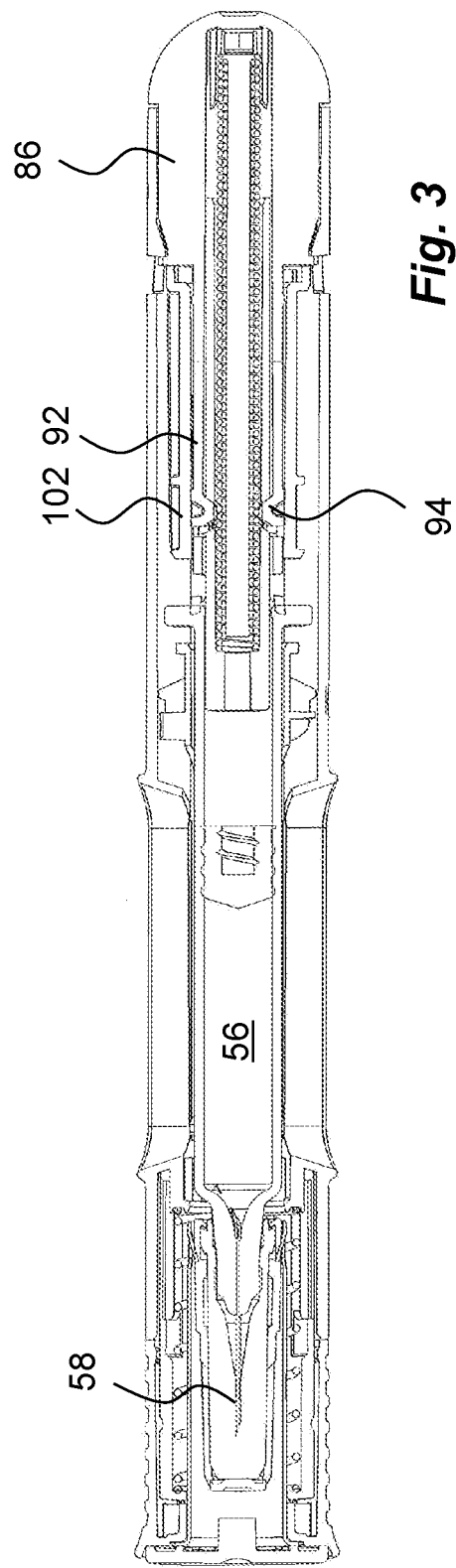
FIG. 3 is a cross-sectional view of the medicament delivery device of FIG. 1.

The medicament delivery device 10 shown in the drawings comprises a generally tubular housing 12 having a proximal end 14 and a distal end 15. Inside the housing a generally transversal wall 16 is arranged, FIG. 3, which wall 16 is provided with a central passage 18. Cut-outs 20 are further arranged on opposite sides of the passage 18. A seat 22 is surrounding the passage 18. Further generally rectangular windows 24 are arranged in the housing, which windows 24 are arranged with inwardly directed wall sections 26. The proximal parts of the wall sections 26 are attached to or form part of the transversal wall 16. Further, a number of longitudinally extending ribs 30 are arranged on the inner surface of the housing, having inwardly directed protrusions 32 at the proximal end thereof, the function of which will be described below. Moreover, at the distal area of the housing generally radially flexing tongues 34 are arranged, which tongues 34 are arranged with inwardly extending ledges 36 at their free ends.

Inside the housing a medicament container holder 38 is arranged coaxial. The medicament container holder 38 comprises a generally elongated tubular body 40 having a distal passage 42 and a proximal passage 44. The proximal passage 44 is arranged with an inwardly directed ledge 46 stretching around the circumference. The body 40 is arranged with two elongated slits 48 on opposite sides of the body. One of the slits 48 extends all the way to the proximal end, connecting the slit with the proximal passage, creating a C-shaped appearance when viewing in the distal direction. The circumferential ledge is further arranged with a number of cut-outs 50, three in the embodiment shown, for providing flexibility of the proximal part of the medicament container holder as will be described. The longitudinal sides of the slits 48 are arranged with outwardly directed ledges 52, which ledges 52 are designed to be in contact with inwardly surfaces 54 surrounding the windows 24 of the housing, for providing orientation and rotational fixation in relation to the housing. The medicament container holder 38 is arranged to accommodate a medicament container 56 that in the embodiment shown is a syringe, having an injection needle 58 attached to a proximal end thereof and a stopper 60 of resilient material that is movable inside the tubular body of the medicament container 56.

Figure 1:
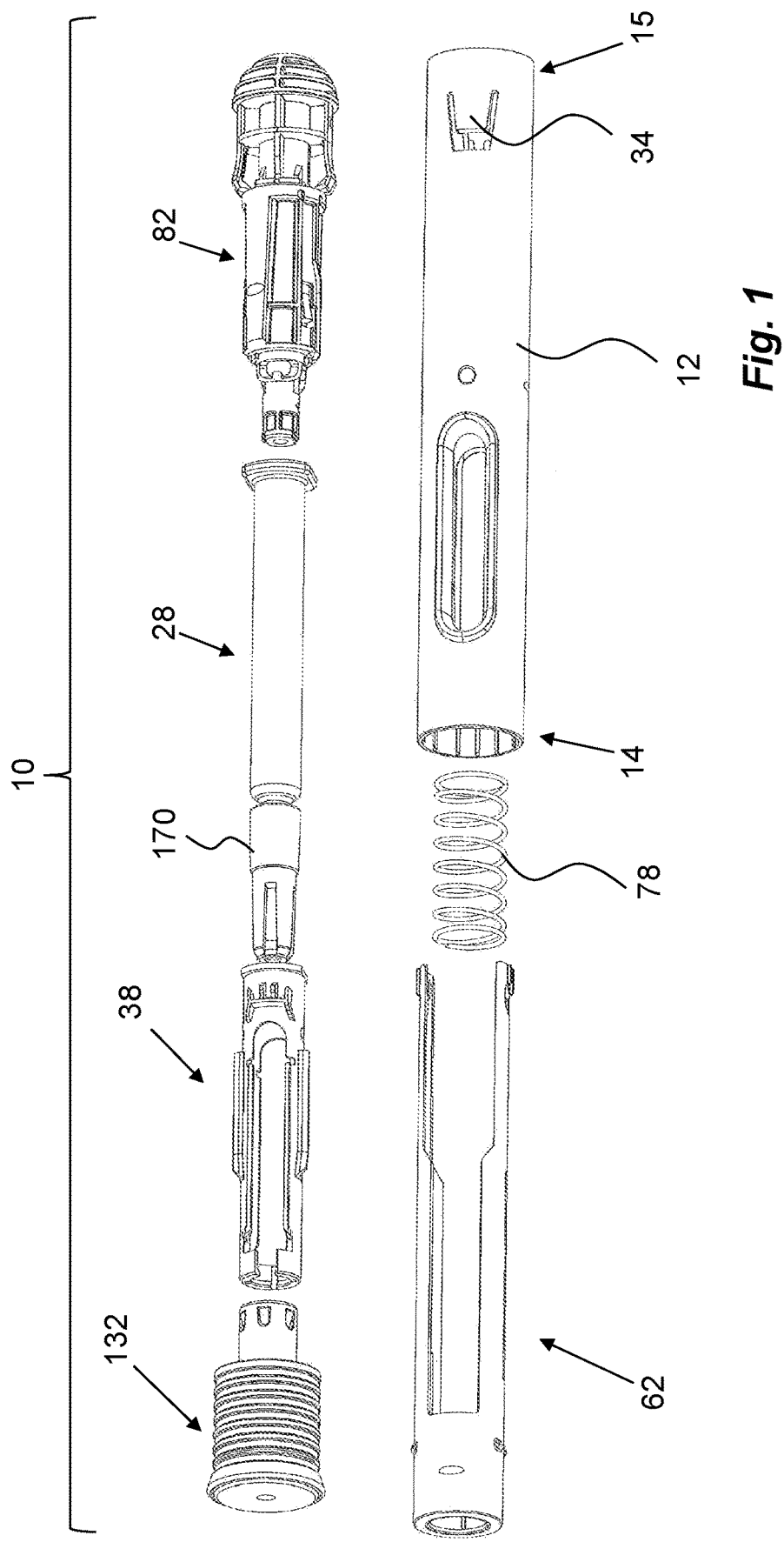
FIG. 1 is an exploded view of a medicament delivery device comprising a protective cap according to the application.
Figure 12:
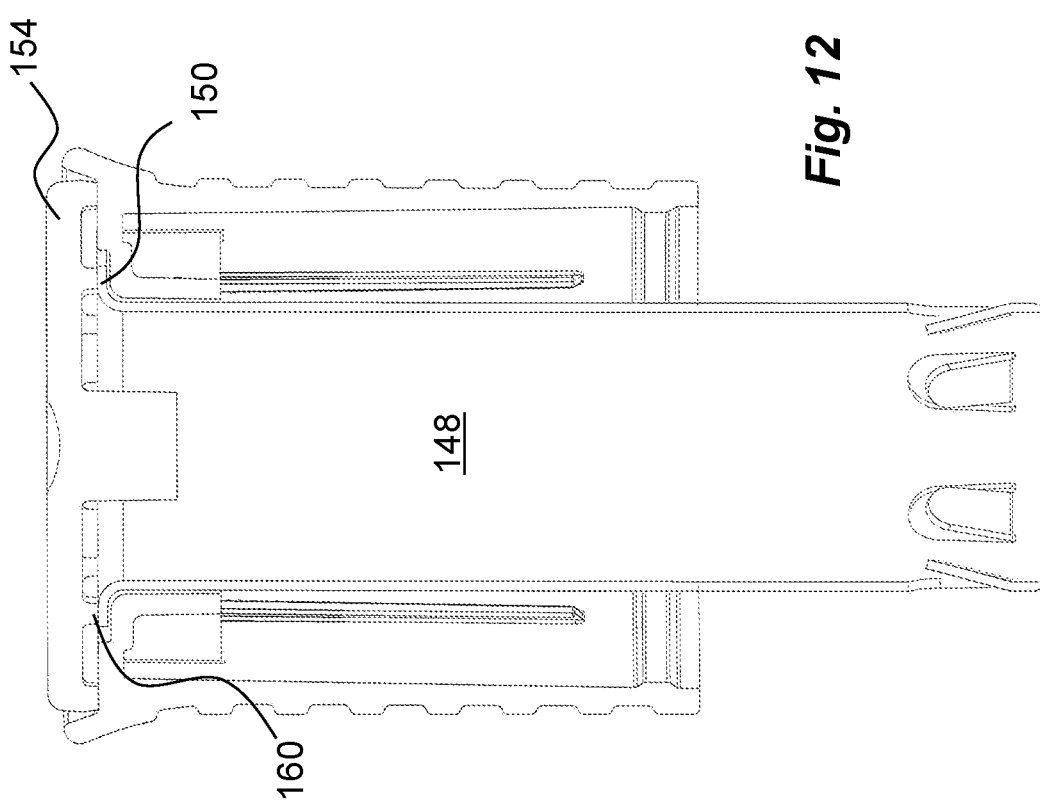
FIG. 12 is a detailed view of components comprised in the medicament delivery device of FIG. 1.

The medicament delivery device further comprises a medicament delivery member guard 62, FIGS. 1 and 5. The medicament delivery member guard 62 comprises a proximal generally tubular body 64 provided with a central passage 66 in a transversal end wall 68. Two oppositely positioned arms 70 are arranged to the distal area of the body 64 and extending in the distal direction. The arms 70 are arranged with longitudinal slits 72 which are to cooperate with the longitudinal ribs 30 of the interior of the housing. At the distal end of the arms 70, outwardly directed ledges 74 are provided. Further on the inner surface of the arms 70, inwardly directed protrusions 76 are arranged, the function of which will be described. A medicament delivery member guard spring 78 is further arranged between a distally directed surface of the transversal end wall 68 of the medicament delivery member guard 62 and a proximally directed surface of the wall 16. In this regard, proximally directed support protrusions 80, FIGS. 3b and 12, are provided on the wall 16 for supporting the medicament delivery member guard spring 78 and preventing it from accidentally interacting with the arms 70 of the medicament delivery member guard 62.

Figure 2:
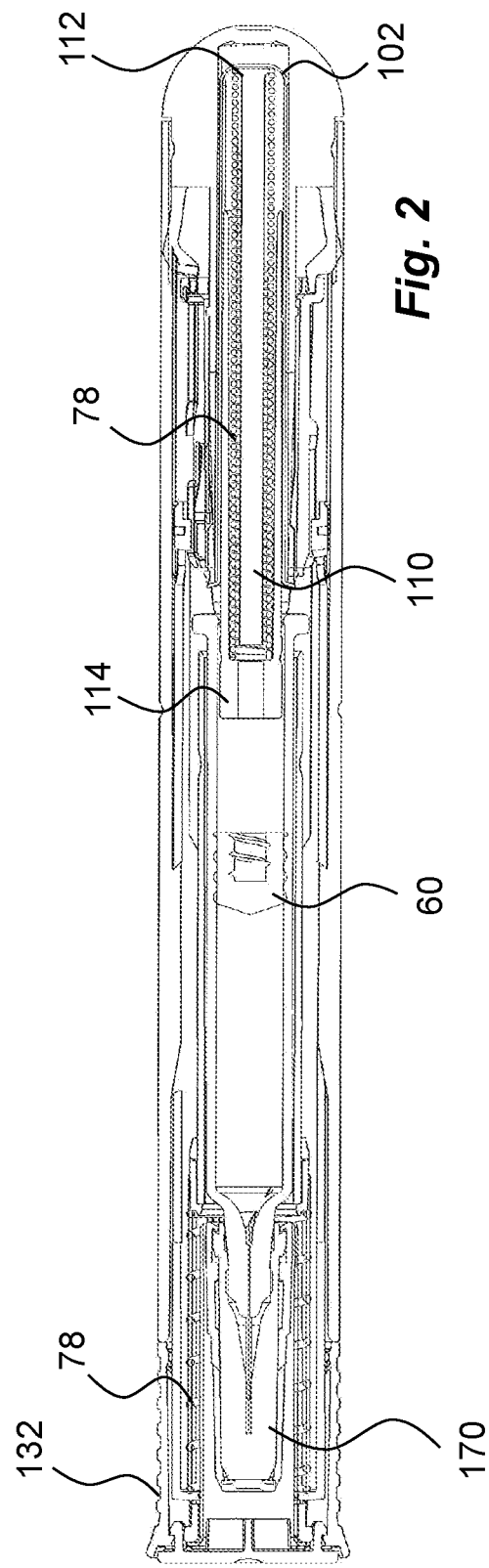
FIG. 2 is a cross-sectional view of the medicament delivery device of FIG. 1.

The medicament delivery device also comprises a power pack or drive unit 82. The power pack 82 comprises an actuator 84 provided with a distal portion forming an end cap 86 of the medicament delivery device when the actuator is connected to the housing. The proximal part of the actuator 84 comprising a generally elongated tubular body 88. A transversal support surface 90 is arranged in the area between the end cap 86 and the body 88, which support surface 90 is designed to cooperate with the ledges 36 of the tongues 34 on the housing 12 for locking the actuator 84 to the housing 12 as seen in FIG. 2b. The body 88 is further arranged with proximally directed arms 92 that are flexible in a generally radial direction. The free ends of the arms 92 are provided with inwardly directed protrusions 94. These inwardly directed protrusions 94 are arranged to fit into and cooperate with recesses 95 in an elongated plunger rod 96, which plunger rod 96 is intended to fit into and be coaxial with the body 88 of the actuator 84.

Further, a drive spring 98 is arranged inside the plunger rod 96 as well as a bracket 100 having a transversal distal part 102 and two proximally extending arms 104 on either side of, and outside, the drive spring 98. The ends of the arms 104 are arranged with outwardly extending ledges 106, which ledges 106 are to be in contact with proximally directed edge surfaces 108 of the body 88 of the actuator 84. Inside the drive spring 98 a guide rod 110 is arranged, provided with a disk 112 at its distal end. The drive spring 98 is thus arranged between a proximal end wall 114 of the plunger rod 96 and the transversal distal part 102 of the bracket 100 via the disk 112 of the guide rod 110, FIG. 2. Further, at the proximal end of the body 88, arc-shaped support elements 116 are arranged, which are flexible in the generally longitudinal direction and are intended to be in contact and support the medicament container 56 in the distal direction.

Moreover, the free ends of the arms 92 of the body 88 are arranged with outwardly directed protrusions 118 that are intended to cooperate with inner surfaces 120 of a generally tubular rotator 122 that is arranged outside and coaxial with the body 88 of the actuator 84. The inner surface 120 of the rotator 122 is arranged with longitudinally extending grooves 124, FIG. 8, the function of which will be described below. The outer surface of the rotator 122 is arranged with guide ledges or ribs 126, where some are extending in the longitudinal direction 126*l* and some are inclined 126*i* in relation to the longitudinal direction as will be explained. Adjacent one longitudinal guide rib 126*l*, a proximally directed tongue 128 is arranged, which tongue 128 is flexible in the generally radial direction, and where the free end of the tongue 128 is arranged with an outwardly directed, wedge-shaped, protrusion 130.

The medicament delivery device is further arranged with a protective safety cap 132, FIGS. 1 and 8, comprising a generally tubular body 134 having a distal passage 136. In order to provide a good fit between the safety cap 132 and the medicament delivery device 10, the inner surface of the body 134 of the safety cap 132 may be arranged with a circumferential ledge 138 function as a first holding element, which ledge 138 is arranged to interact with protrusions 140 function as a second holding element, FIG. 7, on the outer surface of the body 64 of the medicament delivery member guard 62 as seen in FIG. 12. The body 134 of the safety cap 132 is further arranged with a distally directed end surface 135, FIGS. 9 and 12, that acts as an abutment surface against a proximally directed end surface 137, FIGS. 3b and 12, of the housing 12, which end surface 137 also acts as an abutment surface such that the surfaces 135, 137 provide a specific position of the safety cap 132 when mounted onto the medicament delivery device.

Moreover, the body 134 of the safety cap 132 is arranged with a proximal end wall 142, which end wall 142 is arranged with a central circular passage 144. Radially outside the central passage 144 are two oppositely positioned arc-shaped openings 146. A generally tubular medicament delivery member guard remover 148 is to be positioned in the central passage 144 of the end wall 142, wherein the medicament delivery member guard remover 148 will extend into the body 134 of the safety cap 132. The proximal end of the medicament delivery member guard remover 148 is arranged with an outwardly extending ledge 150, which ledge 150 is arranged to be seated in a recess 152 in the end wall 142 of the body 134. The medicament delivery member guard remover 148 is held in place in this position by an end lid 154. The end lid 154 is arranged with distally directed arc-shaped arms 156, provided with radially outwardly directed ledges 158, wherein the arms 156 are designed to fit into the arc-shaped openings 146 of the body 134 and the ledges 158 will snap around edges of the arc-shaped openings 146, locking the end lid 154 to the body 134 of the safety cap 132. The end lid 154 is further arranged with a number of distally directed protrusions or ledges 160 which are to be in contact with the ledge 150 of the medicament delivery member guard remover 148, holding it in place in the recess 152, see FIG. 12.

Figure 13:
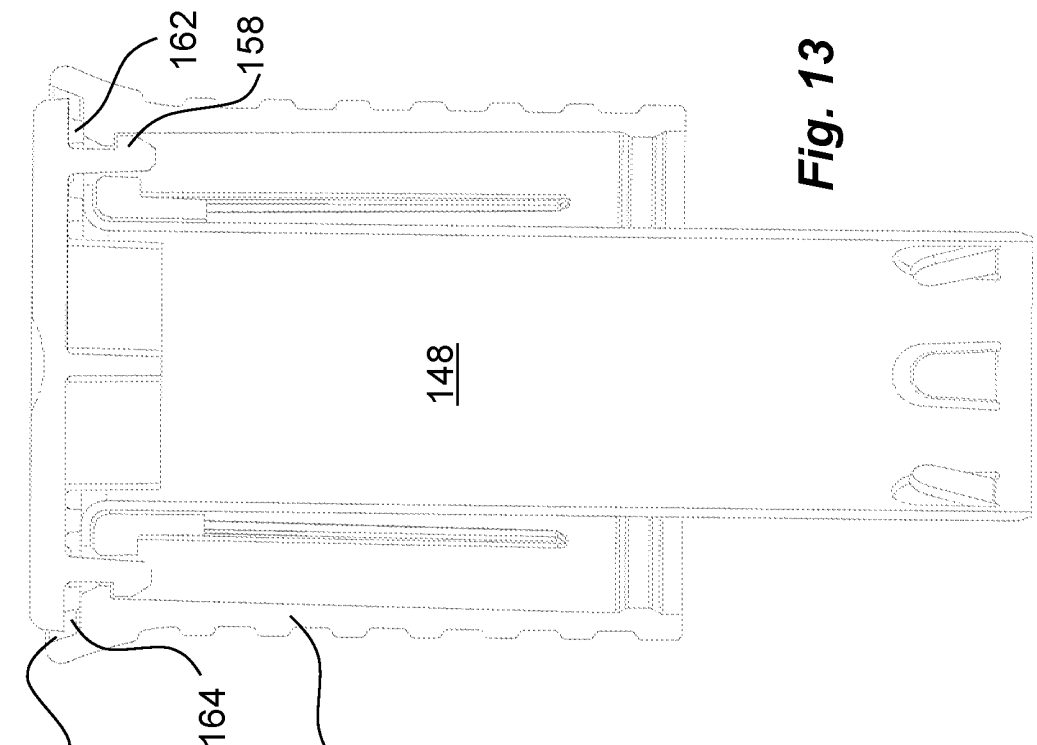
FIG. 13 is a detailed view of components comprised in the medicament delivery device of FIG. 1.
Figure 15:
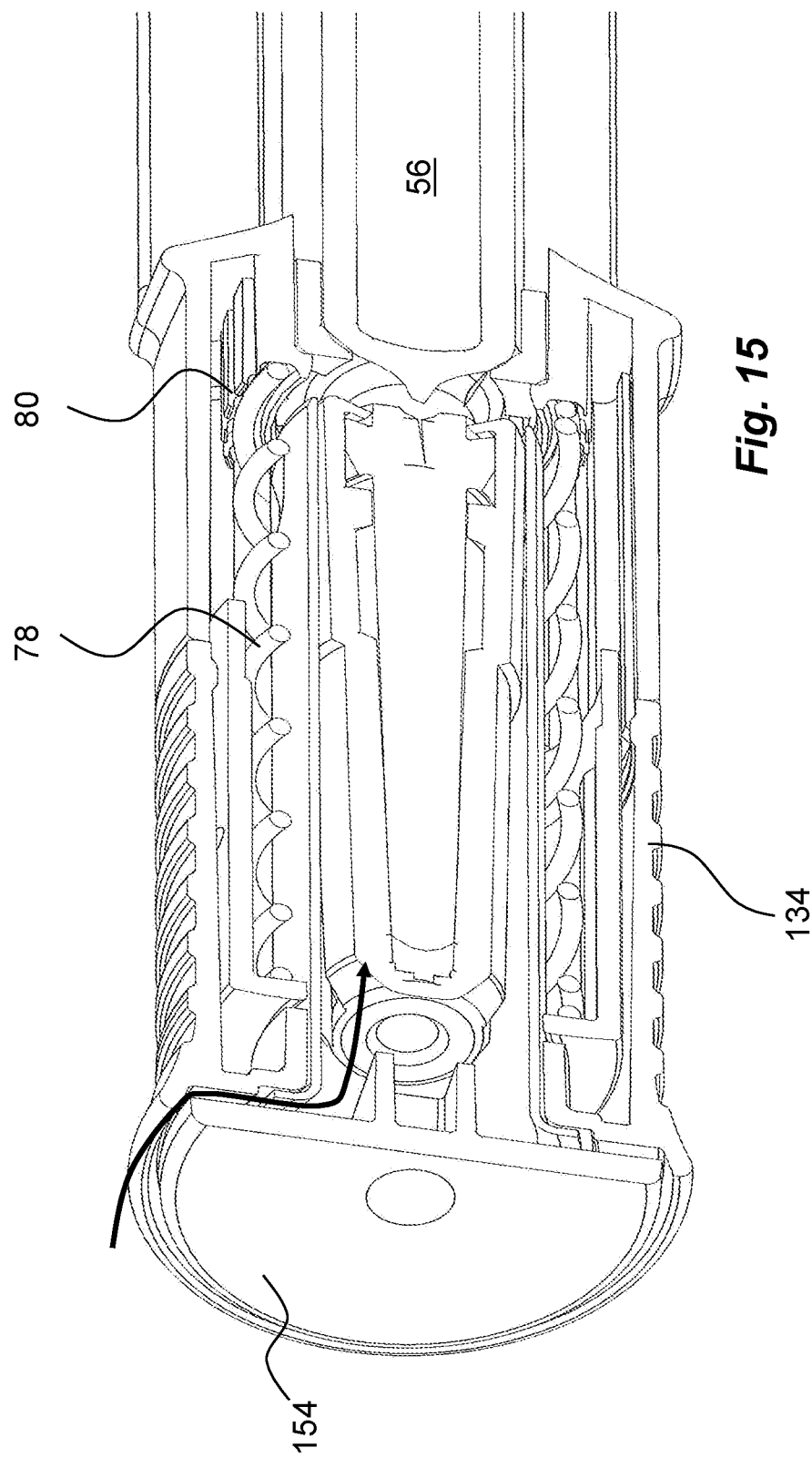
FIG. 15 is a detailed view of components comprised in the medicament delivery device of FIG. 1.
Figure 18:
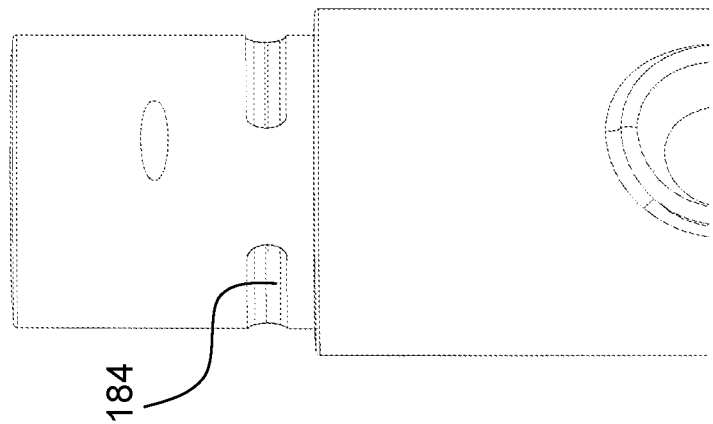
FIG. 18 is a detailed view of components comprised in the medicament delivery device of FIG. 1.

The end lid 154 is arranged with further protrusions 162 as spacers at the edge of the end lid 154 that are in contact with the end wall 142 of the body 134, creating a space 164 between the body 134 and the end lid 154, FIG. 13. The diameter of the end lid 154 is chosen such in relation to the proximal edge of the body 134 such that gaps 166 are created around the circumference. The design provides an air passage through the safety cap 132, as seen by the arrow in FIG. 15, preventing possible suffocation should a child for example put the safety cap 132 in the mouth. Moreover, the distal end of the medicament delivery member guard remover 148 is arranged with generally proximally and inwardly inclined tongues 168 that are designed to be in contact with and engage a medicament delivery member shield 170 such as a rigid needle shield or a flexible needle shield, covering the injection needle 58.

Figure 14:
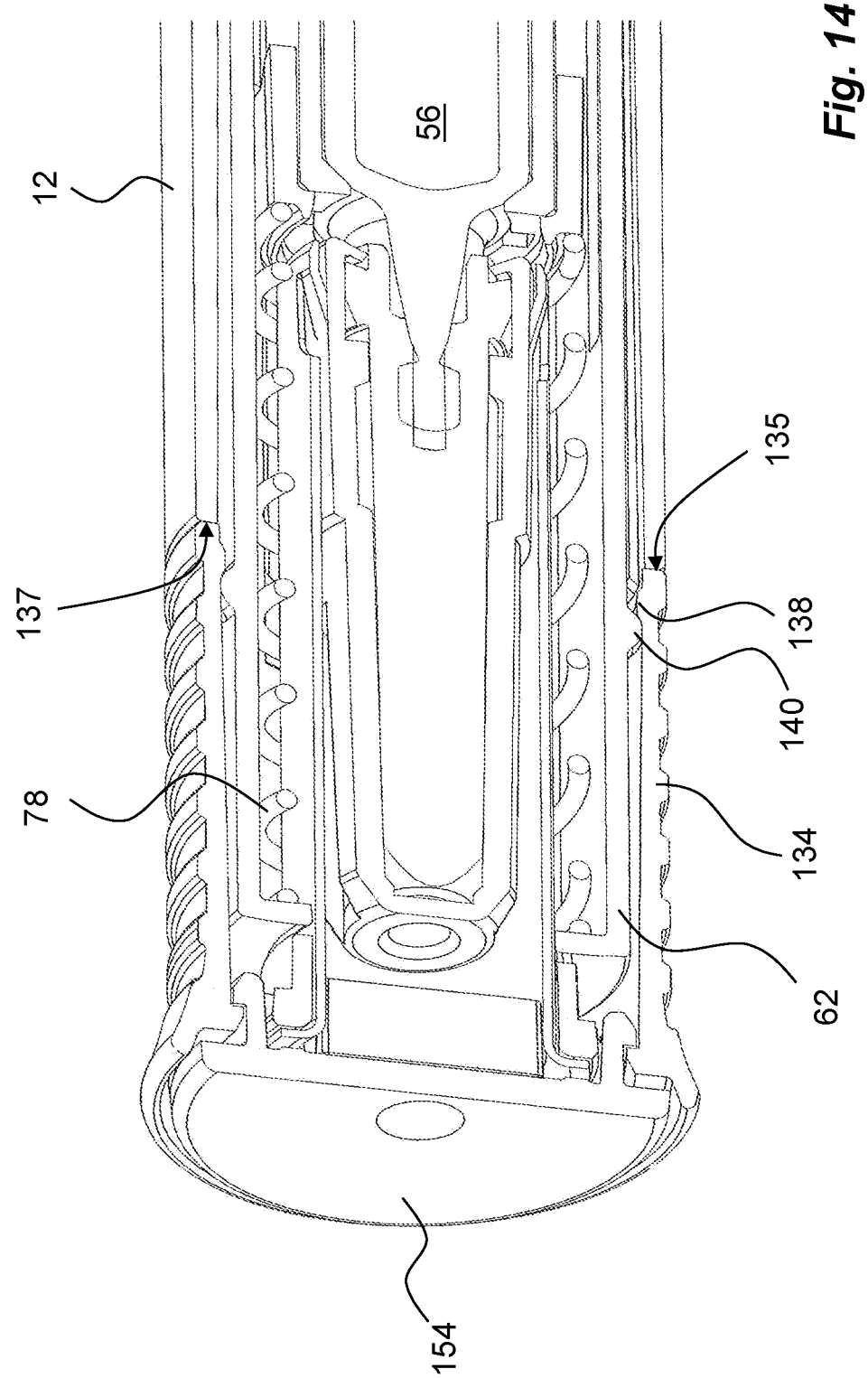
FIG. 14 is a detailed view of components comprised in the medicament delivery device of FIG. 1.

The medicament delivery device 10 according to the drawings is intended to function as follows. The medicament delivery device is delivered to a user with the safety cap 132 attached to the proximal end of the medicament delivery device. The medicament delivery member guard 62 is in an extended position in relation to the housing 12 such that when the abutment surface 135 of the safety cap 132 is in contact with the abutment surface 137 of the housing, the circumferential ledge 138 is distally of, and in contact with, the protrusions 140 of the medicament delivery member guard 62 as seen in FIG. 14. This provides a very secure fit, reducing the risk for premature release of the protective safety cap 132 from the medicament delivery member guard 62 and the medicament delivery device 10.

The medicament delivery device 10 is generally activated by the medicament delivery member guard 62 being pushed into the housing 12 when the proximal end of the medicament delivery device is pressed against a dose delivery site, as will be described. This may happen accidentally if the medicament delivery device is dropped against a hard surface such as a floor. Now there is a risk that the medicament delivery device 10 is activated in that the medicament delivery member guard 62 may be moved in relation to the housing 12 due to the impact forces, which might trigger the medicament delivery device. This risk is reduced and minimized due to the medicament delivery member guard 62 is held by the engagement with the safety cap 132 by the protrusions 140 on the outer surface of the body 64 of the medicament delivery member guard 62 interacting with the ledge 138.

When the safety protecting cap 132 is removed, the medicament delivery member guard remover 148 grips the medicament delivery member shield 170 with its tongues 168, whereby also the medicament delivery member shield 170 is removed. The user may now press the proximal end of the medicament delivery device 10 against the dose delivery site, whereby the medicament delivery member guard 62 is pushed into the housing 12, causing a penetration by the injection needle 58. The movement of the medicament delivery member guard 62 will cause its protrusions 76 at the distal end to slide in relation to the rotator 122. When the protrusions 76 reach the inclined guide ribs 126i of the rotator 122, the rotator 122 will rotate in relation to the actuator 84, which in turn causes the outwardly protrusions 118 of the arms 92 of the actuator 84 to be moved in position with the longitudinal grooves 124 on the inner surface 120 of the rotator 122. The arms 92 are thereby free to move radially outwards, whereby the engagement between the inwardly directed protrusions 94 and the recesses 95 of the plunger rod 96 is removed, releasing the plunger rod 96. The plunger rod 96 is then urged in the proximal direction by the force of the drive spring 98. The plunger rod 96 will now act on and move the stopper 60 of the medicament container 56 in the proximal direction, expelling a dose of medicament through the injection needle 58. At the end of the injection sequence, the distal end of the plunger rod 96 will pass the bracket 100 whereby the arms 104 of the bracket 100 are free to move radially inwards, wherein the ledges 106 are moved out of contact with the surfaces 108 of the actuator 84. Because the distal end of the drive spring 98 is in contact with the transversal distal part 102 of the bracket 100 via the disk 112 of the guide rod 110 and since the drive spring 98 has a residual force, the bracket 100 will be forced suddenly in the distal direction until the distal end of the bracket 100 hits an end wall of the actuator 84, causing a tactile and audible signal to the user that the injection sequence is completed and that it is safe to remove the medicament delivery device from the dose delivery site.

The user can now remove the medicament delivery device 10 whereby the medicament delivery member guard 62 is pushed in the proximal direction by the medicament delivery guard spring 78. This will cause the protrusions 76 of the medicament delivery member guard 62 to move such that they come in contact with and pass the wedge-shaped protrusions 130 of the tongues 128 of the rotator 122. The passing of the protrusions 130 will cause a locking of the medicament delivery member guard 62 in the extended position, covering the medicament delivery member 58, in turn preventing accidental injuries on the medicament delivery member 58. The medicament delivery device can now be discarded.

Figure 17:
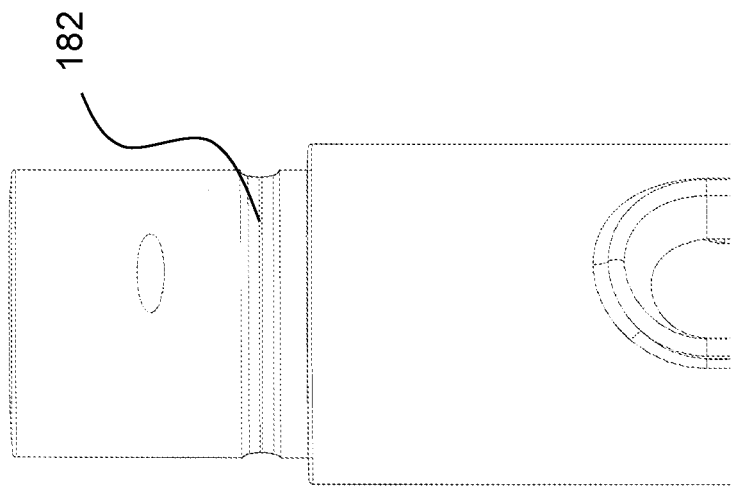
FIG. 17 is a detailed view of components comprised in the medicament delivery device of FIG. 1.
Figure 16:
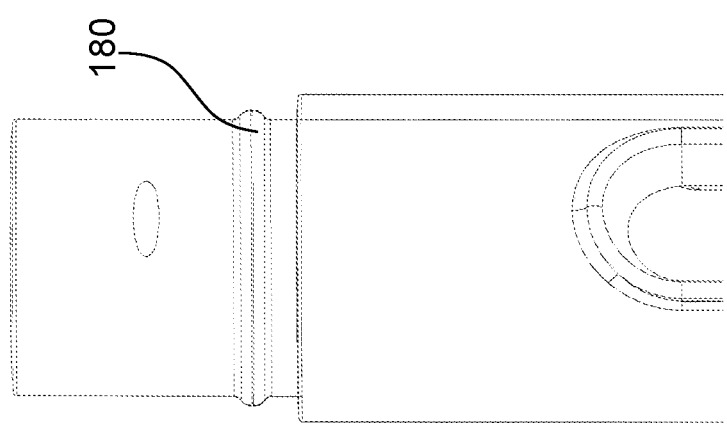
FIG. 16 is a detailed view of components comprised in the medicament delivery device of FIG. 1.
Figure 21:
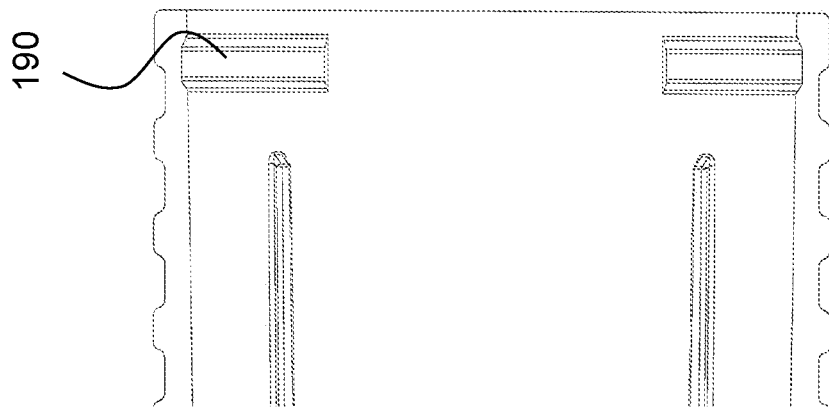
FIG. 21 is a detailed view of components comprised in the medicament delivery device of FIG. 1.
Figure 20:
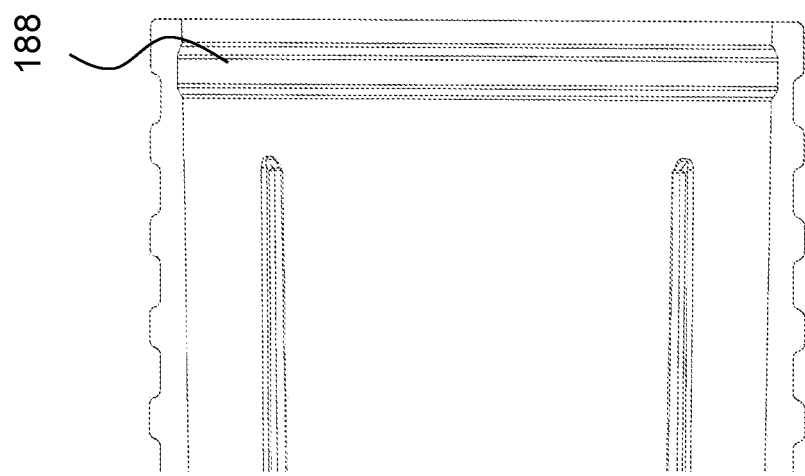
FIG. 20 is a detailed view of components comprised in the medicament delivery device of FIG. 1.
Figure 19:
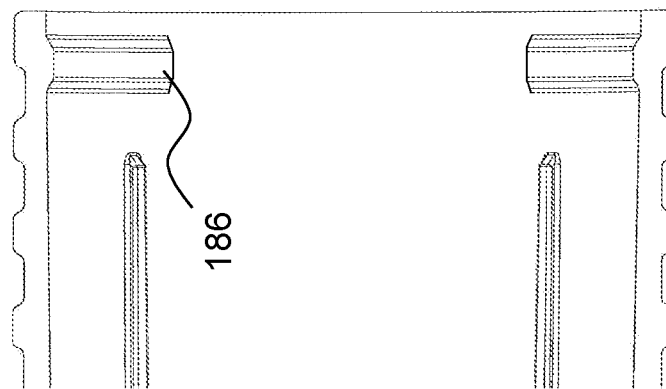
FIG. 19 is a detailed view of components comprised in the medicament delivery device of FIG. 1.

Regarding the securing of the medicament delivery member guard 132 it is to be understood that several other alternatives are feasible. Instead of discrete protrusions on the outer surface of the medicament delivery member guard, there could for example be a continuous protrusion 180 running along the circumference as seen in FIG. 16. As an alternative, there could be a recess in the medicament delivery member guard and protrusions on the inner surface of the body of the safety cap. It is to be understood that the recesses in the medicament delivery member guard could either be continuous 182 as seen in FIG. 17 or discrete 184 as seen in FIG. 16. As a further alternative, the protrusion on the inner surface of the safety may be discrete 186 instead of continuous, FIG. 19. As yet an alternative there may be recesses on the inner surface of the safety cap, either continuous 188, FIG. 20 or discrete 190, FIG. 21. As understood there are many variants that may be combined in order to obtain the desired function of enhanced safety against accidental activation.

It is to be understood that the embodiment described above and shown in the drawings is to be regarded only as a non-limiting example that may be modified in many ways within the scope of the patent claims.

The invention claimed is:

1. A protective cap to be releasably connected to a medicament delivery device, wherein the medicament delivery device comprises an activator element at a proximal end thereof, the protective cap comprising:
   a generally tubular body arranged with a proximal end wall;
   a first holding element arranged on an inner surface of the generally tubular body, wherein the first holding element designed to interact with second holding element arranged on an outer surface of the activator element of the medicament delivery device; and
   a lid including a plurality of distally directed arms provided with radially outwardly directed ledges to thereby attach the lid to the proximal end wall of the generally tubular body, wherein a diameter of the lid is chosen in relation to a proximal edge of the generally tubular body such that a gap is created around a circumference of the lid, wherein the lid includes protrusions at an edge of the lid that are in contact with the proximal end wall of the generally tubular body to thereby form air passages through the protective cap when the lid is attached to the proximal end wall of the generally tubular body, and wherein the air passages are of a sufficient size to mitigate a risk of suffocation if the protective cap is positioned in a mouth.

2. The protective cap according to claim 1, wherein the first holding element comprises a protruding element and the second holding element comprises a protruding element.

3. The protective cap according to claim 1, wherein one of the first and the second holding elements comprises a protruding element and the respective the other one of the first and the second holding element comprise a recess element.

4. The protective cap according to claim 2, wherein the first or the second protruding elements comprise discrete elements.

5. The protective cap according to claim 2, wherein the first or the second protruding elements comprise continuous elements.

6. The protective cap according to claim 1, further comprising a medicament delivery member guard remover, attached to the body and held in position by the lid.

7. A medicament delivery device, comprising the protective cap according to claim 1.

* * * * *